(12) United States Patent
Thordarson et al.

(10) Patent No.: US 6,623,545 B2
(45) Date of Patent: Sep. 23, 2003

(54) LIQUID-LIQUID EXTRACTION DEVICE AND ON-LINE TRANSFER TO A GAS CHROMATOGRAPHY APPARATUS

(75) Inventors: Eddie Thordarson, Lund (SE); Jan Norberg, Fredriksberg (DK)

(73) Assignee: Esytech AB, Lund (SE)

(*) Notice: Subject to any disclaimer, the term of this patent is extended or adjusted under 35 U.S.C. 154(b) by 0 days.

(21) Appl. No.: 10/132,711

(22) Filed: Apr. 26, 2002

(65) Prior Publication Data

US 2002/0189447 A1 Dec. 19, 2002

Related U.S. Application Data

(63) Continuation of application No. PCT/SE00/02104, filed on Oct. 27, 2000.

(51) Int. Cl.[7] .................. B01D 53/22; B01D 15/08
(52) U.S. Cl. .................. 95/45; 95/82; 95/89; 96/8; 96/10; 96/105
(58) Field of Search .................. 95/44, 45, 50, 95/82, 89; 96/5, 8, 10, 101, 105

(56) References Cited

U.S. PATENT DOCUMENTS

| | | | | |
|---|---|---|---|---|
| 1,685,759 A | * | 9/1928 | Walter | |
| 2,223,586 A | * | 12/1940 | Thomas | |
| 3,367,850 A | * | 2/1968 | Johnson | |
| 3,371,468 A | * | 3/1968 | Shropshire | |
| 3,721,065 A | * | 3/1973 | Robicheaux et al. | 55/67 |
| 4,734,112 A | * | 3/1988 | Okita et al. | 55/158 |
| 4,750,918 A | * | 6/1988 | Sirkar | 55/16 |
| 5,013,436 A | * | 5/1991 | Lee et al. | 210/321.8 |
| 5,135,547 A | * | 8/1992 | Tsou et al. | 55/16 |
| 5,281,254 A | * | 1/1994 | Birbara et al. | 95/44 |
| 5,749,941 A | * | 5/1998 | Jansen et al. | 95/44 |
| 5,876,486 A | * | 3/1999 | Steinwandel et al. | 95/44 |
| 5,954,858 A | * | 9/1999 | Peretti et al. | 95/44 |
| 5,993,515 A | * | 11/1999 | Sirkar | 95/46 |
| 6,042,787 A | * | 3/2000 | Pawliszyn | 422/69 |
| 6,093,371 A | * | 7/2000 | Wilson | 422/89 |
| 6,156,096 A | * | 12/2000 | Sirkar | 95/44 |
| 6,165,253 A | * | 12/2000 | Sirkar et al. | 96/6 |

FOREIGN PATENT DOCUMENTS

SE    ES 2103224 A1    9/1997

OTHER PUBLICATIONS

J.R. Veraart et al., "Coupling of biological sample handling and capillary electrophoresis", Journal of Chromatography A. 856 (1999) pp 483–514.

J.A. Jonsson et al. "Automated system for the trace analysis of organic compounds with supported liquid membranes for sample enrichment", Journal of Chromatography A. 665 (1994) pp 259–268.

Yin Shen et al., "On–Line Microporous Membrane Liquid–Liquid for Sample Pretreatment Combined with Capillary Gas Chromatograph Applied to Local Anesthetics in Blood Plasma", Analytical Chemistry, vol. 70(5), pp. 946–953 Mar.1998.

* cited by examiner

Primary Examiner—Robert H. Spitzer
(74) Attorney, Agent, or Firm—Harness, Dickey & Pierce, P.L.C.

(57) ABSTRACT

An extraction device for liquid—liquid extraction of at least one analyte from a sample and on-line transfer of the analyte(s) to a gas chromatography extraction unit, a sample inlet, a sample outlet, and an organic liquid inlet, wherein the extraction device also includes a needle to be connected with a gas chromatography apparatus injector for the on-line transfer of the analyte(s) from the membrane-based extraction unit to the gas chromatography apparatus via the needle, an organic liquid being immobilized as a stagnant phase in a volume of less than 20 $\mu l$ in the membrane-based extraction unit.

33 Claims, 1 Drawing Sheet

Figures 1, 2:
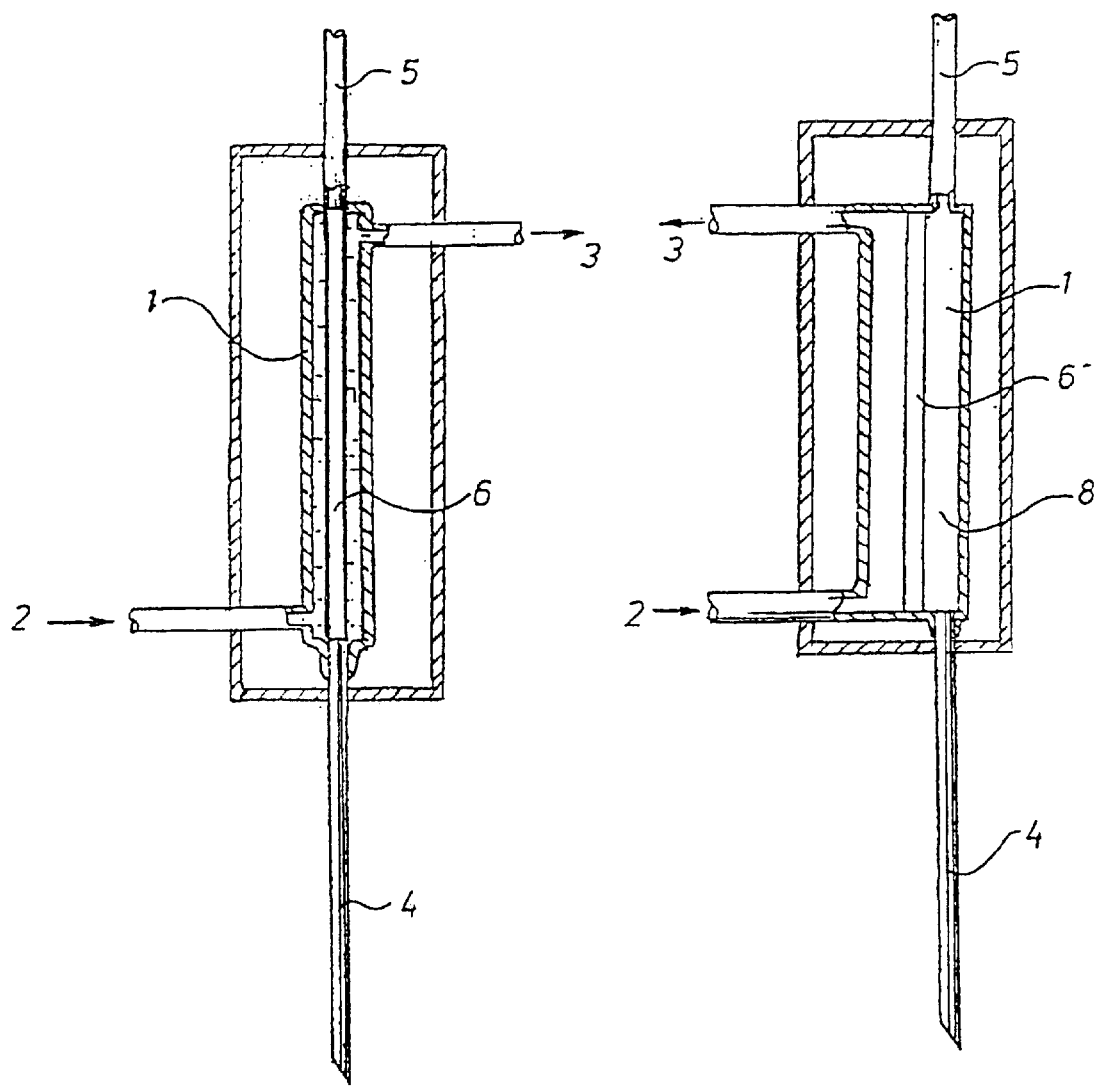

LIQUID-LIQUID EXTRACTION DEVICE AND ON-LINE TRANSFER TO A GAS CHROMATOGRAPHY APPARATUS

This application is a continuation of co-pending PCT International Application No. PCT/SE00/02104, filed on Oct. 27, 2000, the entire contents of which are hereby incorporated by reference and for which priority is claimed under 35 U.S.C. §120; and this application claims priority of Application No. 9903886-1 filed in Sweden on Oct. 27, 1999 under 35 U.S.C. §119.

BACKGROUND OF INVENTION

The present invention relates to a liquid—liquid extraction device for extraction of at least one analyte from a sample and on-line transfer of said analyte(s) to a gas chromatography apparatus, and to a method in which the extraction device is used.

BACKGROUND ART

In the preparation of samples before gas chromatography analysis, several techniques are known. One of the most suitable techniques used at present is an LLE (liquid—liquid extraction) operation before the gas chromatography analysis. However, this technique is associated with several disadvantages. First, large volumes of the solvent for extraction are required, which is hazardous for the operator and the environment. Further, this technique is expensive, the operations are laborious and automatisation is difficult. Moreover, this technique rarely allows for anything but off-line operations with a concomitant risk of sample contamination. Emulsion formation and waste problems are also associated with this technique, as well as difficulties in handling small sample volumes.

Another useful technique is SPE (Solid Phase Extraction). One of the major problems of this technique is that it includes a complicated phase exchange before the gas chromatography (GC) analysis. Another problem is that it suffers from break-through and this effect is more or less pronounced depending on the sample matrix. Moreover, the SPE technique is associated with the same problems as the LLE technique, even though the emulsion formation problems and the automatisation difficulties are not as pronounced for the SPE technique.

A fairly new technique is SPME (Solid Phase Micro Extraction) coupled to gas chromatography. Although the SPME technique is considered to be increasingly utilized in the future, it suffers from several shortcomings. In this technique, a rigid glass fibre, either bare or covered with a suitable stationary phase, is contacted with the sample in the extraction step. This technique involves several phase conversions, i.e. from gas to liquid and then to gas again. Thus, the analytes are distributed between the sample liquid and the air gap above the sample where the sampling takes place (head-space analysis). With a view to increasing the amount of analytes in the gas phase, the sample is often heated. Subsequently, the analytes are distributed between the gas phase and the liquid on the glass fibre. Further, the glass fibre has to be transferred to the GC injector after the extraction step. When the glass fibre is inserted in the injector, the analytes are to be desorbed from the fibre and transferred to the gas phase without the evaporation of the extracting medium (the liquid). This is often done manually, but can be automatised. The desorption operation must preferably take place very quickly. In cases where the SPME glass fibre is used for extraction into an aqueous medium, the fibre is dipped in the sample solution which is shaken, or the fibre is rotated.

A further disadvantage of the SPME technique is that the extraction unit, i.e. the fibre covered with liquid and enclosed in a syringe, is not stationarily enclosed in the syringe and has to be handled outside the analysis system during the analysis.

The SPME technique is also time-consuming and the time period until equilibrium can amount to several hours. This technique is also highly sample-matrix dependent, which can reduce the analyte capacity and causes a risk of fouling of the stationary phase. Also, the equilibrium constants may vary between samples. Problems have also been encountered with the reproducibility, the repeatability (RSD 1–92%) and the linearity (fouling and memory effects). Further, the fibres are mechanically and thermally sensitive, and air bubbles-may occur at the surface when the liquids are analysed. The SPME technique is also relatively expensive.

Still another extraction technique is MMLLE (Microporous Membrane Liquid—Liquid Extraction). This technique resembles the technique according to the present invention, but differs in several important aspects. The organic liquid in the MMLLE technique is continuously moving during the extraction step. Further, the sample injection volume is very large. MMLLE C necessitates additional extraction hardware as it involves two liquid chromatography injectors and an intermediate transfer of the extract (organic liquid containing analytes) to a loop, thereby causing a more dispersed (diluted) sample, and potential analyte losses, and it makes handling of small sample volumes impossible. Moreover, a so-called "retention gap" complicates the GC analysis, i.e. the gas chromatograph has to be modified in some respects when applied to the MMLLE technique. Finally, the transfer of the extract in this technique is performed by a gas pressure being exerted by the support gas flow in the gas chromatograph which is another GC modification.

SUMMARY OF THE INVENTION

The object of the present invention is to solve the above-mentioned problems described in connection with the background art.

This object is achieved by a liquid—liquid extraction device and a method for extraction of the type described by way of introduction and which are further defined in the characterising part of claim 1 and the independent method claim. Other embodiments are defined in the subclaims. Other objects and advantages will be apparent from the detailed description of the invention and the appended claims.

The present invention will now be described in more detail with reference to the accompanying drawings, in which FIG. 1 is a schematic view of an extraction device according to the present invention, in which the membrane-based extraction unit (1) is a porous hollow fibre membrane.

FIG. 2 is a schematic view of an extraction device in which the membrane-based extraction unit (1) is a flat membrane.

The term "stagnant phase" used herein means that the phase is only temporarily present in the membrane-based extraction unit 1, i.e. it is not stationary therein, as it is displaced to the gas chromatograph and replaced by new organic liquid constituting the stagnant phase.

The term "gas chromatography compatible" used herein in connection with the analytes and the organic liquid means that the analytes in the sample can be properly separated in the gas chromatograph and that the organic liquid will be tolerated by the gas chromatograph.

The extraction device according to the present invention comprises at least one membrane-based extraction unit 1, a sample inlet 2, a sample outlet 3, an organic liquid inlet 5, a membrane 6 and a needle 4 to be inserted in a gas chromatography injector 7. The membrane-based extraction unit 1 is a liquid—liquid extraction unit.

The extraction device and the method in which this is utilised are new and possess several substantial advantages compared to related known techniques. The extraction device according to the present invention offers automatisable on-line extraction and subsequent gas chromatography analysis of very small sample volumes. Further, small amounts of solvent (organic, liquid) are consumed, and the extraction device is easy to handle, is safe and requires a minimum of manual handling. Further, injection of the whole stagnant phase is possible. Other differences compared to known technique are that the matrix (sample) dependence is reduced and that no phase transfer has to be performed before the gas chromatography analysis. Further, the extraction device according to the present invention offers higher capacity compared to known techniques, and the time period required for the sample preparation (extraction) is very short, which means that there are no problems to keep the extraction time below the time period required for the GC analysis of the extract. Thus, all of the problems and disadvantages associated with the above described LLE and SPE techniques have been eliminated in the present invention.

Compared particularly to the SPME technique, the present invention offers several substantial advantages. For example, no distribution of analyte between liquid and gas is required, nor any heating step. Further, according to the present invention the whole sample (analyte in organic liquid) is evaporated in the gas chromatograph (no heating capacity problem). Further, no shaking of the fibre is necessary, and no physical adsorption takes place. Moreover, the membrane in the extraction unit 1 according to the present invention is all the time enclosed in the extraction device. Other important differences are that according to the present invention the sample preparation takes place in a flow system, and the phase in which the sample is enriched is injected directly into the gas chromatograph.

Further, a specific difference between the extraction device and the method according to the present invention compared to the MMLLE technique is that the organic liquid, corresponding to the solvent, is stagnant according to the invention. Further, the sample injection volume is more than 50 times smaller than in MMLLE. Moreover, the gas chromatography apparatus does not have to be modified to be applicable to the present invention, as is the case with the MMLLE technique. Instead, the extraction device according to the present invention is directly applicable to any conventional gas chromatograph without any apparatus modifications.

Moreover, the extraction device according to the present invention is also unique as to the construction. The miniaturised device including a needle 4 has been optimised by the inventors in a surprising way to fulfill the requirements for an automatisable, fast on-line extraction-gas chromatography analysis of small sample volumes.

The sample liquid containing the analytes can be any physiological liquid, e.g. chosen from the group consisting of whole blood, urine, sweat, plasma, serum, nasal secrete, cerebrospinal fluid and other liquids from living organisms. It can also be a non-physiological liquid, e.g. a liquid chosen from the group consisting of river water, sea water, lake water, effluent water, influent water, drinking water or a dispersion of any solid matter in aqueous solution, e.g. soil samples, food samples, plant samples, tissue samples or aqueous samples of dissolved airborne compounds. The sample volume is small and is between about 20 $\mu$l, more often 100 $\mu$l, and about 20 ml, preferably between 0.3 and 5 ml. Volumes outside the above-defined range may also be applicable, however in rare cases.

The analytes of interest in said sample have to be gas chromatography compatible and are chosen from the group consisting of volatile organic compounds, preferably benzene, toluene, and xylene; polyaromatic hydrocarbons, polychlorinated and polybrominated biphenyls, volatile biocides, fatty acids and fats.

The organic liquid, acting as a "solvent" and serving as a stagnant phase, has to be gas chromatography compatible and is a hydrophobic organic liquid chosen from the group comprising alcohols, preferably octanol; saturated, volatile straight-chain branched or cyclic hydrocarbons, preferably pentane, hexane, heptane or cyclopentane, cyclohexane, cycloheptane; partially unsaturated volatile straight-chain, branched or cyclic hydrocarbons, preferably heptene or cyclohexene; ethers, such as diethylether, dihexylether; carbon disulphide, and carbon tetrachloride.

Thus, all analytes in the liquid samples which are soluble in both types of liquids can be analysed by using the extraction device according to the present invention, particularly small molecules (<1 kDa) which are or which can be uncharged. Preferably, only one membrane 6 is included in the membrane-based extraction unit 1, either in the form of a hollow fibre membrane, or in the form of a flat membrane, through which the extraction takes place.

Referring to FIG. 1 illustrating a hollow fibre membrane, i.e. one embodiment of the present invention, the membrane-based extraction unit 1 is preferably essentially cylindrical and vertically arranged. Further, the sample outlet 3 and the organic liquid inlet 5 are preferably positioned in the upper end of the unit, whereas the sample inlet 2 and the organic liquid outlet, which is directly connected to the needle 4, preferably are located in the lower end of the unit. Thus, the cylindrical hollow fibre part of the membrane-based extraction unit 1 is surrounded by a preferably cylindrical, concentric space through which the sample liquid is passed. The porosity may vary between 0 and 90%, preferably between 40 and 85%. The average pore size is 0–10 $\mu$m, preferably about 0.01–0.5 $\mu$m. The inner diameter of the hollow fibre membrane is 10–500 $\mu$m, preferably 100–330 $\mu$m.

The organic liquid serving as a stagnant phase is located, more precisely immobilised, within the fibre structure, and the sample liquid passes along the exterior of the fibre structure. The sample liquid is continuously fed by a liquid delivery device, also called a pump device, via the sample inlet 2 to the exterior of the fibre, which means that new analytes in the sample liquid are continuously contacted with the hollow fibre membrane surface. Thus, the analytes of interest are accumulated in the hydrophobic organic liquid, and the concentrations thereof are increasing with the time.

Referring to FIG. 2 illustrating a flat membrane, i.e. another embodiment of the present invention, the sample liquid and the organic liquid are present on opposite sides of the vertically arranged flat membrane 6 in equally formed channels. Also in this case, the sample liquid is continuously fed to the membrane-based extraction unit 1 via a sample inlet 2. Preferably, the sample inlet 2 and the fixation of the needle 4 are arranged in the lower end of the extraction device, whereas the sample outlet 3 and the organic liquid inlet 5 are located in the upper end of the extraction device. When the sample is fed via the sample inlet 2 upwardly along the exterior surface of the flat membrane 6, analytes diffuse through the membrane into the organic liquid which constitutes the stagnant phase 8 in the organic liquid channel and which is immobilised in the flat membrane structure. The flat membrane thickness may vary between 10 $\mu$m and 500 $\mu$m, preferably between 25 $\mu$m and 200 $\mu$m. The same porosity and average pore size as for the hollow fibre membrane also apply to the flat membrane.

The membranes used in the present invention are conventional and may be hydrophobic or hydrophilic, preferably hydrophobic. Examples of hydrophobic membranes are polytetrafluoroethylene (PTFE), polyvinylidenedifluoride (PVDF), polypropylene (PP), polyethylene (PE), and silicone rubber. These membranes are preferably, but not necessarily, provided with a stabilizing backing. The sample liquid containing the analytes and the organic liquid serving as a stationary phase in the hydrophobic membrane-based extraction unit 1 are separated by the porous membrane, serving as a phase separator, thereby facilitating the interaction, i.e. the analyte transfer, between-the two liquids in question (interfacial support). In the membrane pores, the organic liquid is immobilised, and the diffusion of selected analyte from the sample liquid takes place into and through these pores of the membrane.

In a hydrophilic membrane, which lacks the immobilized organic liquid constituting the stagnant phase, the hydrophilic sample liquid enters and fills up the pores, and the analytes of interest are further transferred to the stagnant phase outside the membrane structure. Examples of hydrophilic membrane materials are cellulose, polyethersulfone, polysulphone, polyacrylonitrile, and polycarbonate. Otherwise, the physical characteristics (porosity, pore size, thickness) for the hydrophilic membranes are the same as for the hydrophobic membranes.

The extraction device as such, defining the membrane-based extraction unit 1 and the sample and organic liquid conduits and necessary liquid delivery devices may have any convenient shape and be made of any suitable material, e.g. PEEK (polyether-etherketone), PTFE (polytetrafluoroethylene), polypropylene, polyethylene, or stainless steel.

After having passed the membrane-based extraction unit 1, the sample liquid, from which the analytes of interest have been extracted and collected into the hydrophobic organic liquid, is exhausted through the sample outlet 3.

The extraction device according to the present invention also comprises an organic liquid inlet 5 for feeding the organic liquid into the membrane-based extraction unit 1 via a pump device. Moreover, a pump device is used for feeding the sample through the extraction device, i.e. in through the sample inlet 2 and out of the sample outlet 3. Preferably, syringe, reciprocating, or peristaltic pumps are used.

As appears from FIG. 1 and FIG. 2, the extraction device according to the present invention also comprises a protruding needle 4 to be connected with a gas chromatography injector 7. The needle 4 may be integral with the extraction device, or may be screwed or fixed to the extraction device by other means. An O-ring may be used around the fixation part of the needle as a tightening means. The length, outer diameter, inner diameter (bore diameter) and material of the needle 4 are not of particular relevance and may vary as long as the needle is insertable in any conventional gas chromatography injector. Normally, the needle as such is commercially available, but it has been specifically connected to the extraction device by the inventors. The bore of the needle is at its base arranged in direct, open connection with the organic solvent in the lower end of the membrane-based extraction unit 1. Thus, when the membranebased extraction unit 1 as an initial step is provided with the organic liquid volume desired, e.g. about 2×20 $\mu$l in increments, the needle bore will be filled essentially down to the tip with the organic liquid. During the sample flow through the extraction unit, analytes of interest are accumulated in the organic liquid. When the flow of sample liquid through the membrane-based extraction unit 1 has been stopped, i.e. when the extraction operation is over, i.e. after 1–60 mm, more often after 5–30 mm, mostly after 15–20 mm, the whole extraction device including the needle 4 is pneumatically lowered until the needle 4 has penetrated the septum of the gas chromatography injector 7. The stagnant phase containing the analytes is then displaced via a pump device into the needle 4 and further down to the gas chromatograph injector by introducing additional organic liquid via the inlet 5 therefor. When all of the analytes in the membrane-based extraction unit 1 and the needle 4 have been displaced to the gas chromatograph, the extraction unit and the needle 4 will contain pure organic liquid, i.e. they have been regenerated and are ready for a new sample flow. Optionally, an intermediate washing step is included.

The separation of the analytes takes place in a conventional gas chromatograph. The detection of the separated analytes is normally achieved by any suitable GC detector, preferably a FID, ECD or a mass spectrometer.

The whole analysis operation or parts thereof including the steps of feeding the extraction unit 1 with organic liquid and sample, the sample flow interruption, the regeneration of the stagnant phase with fresh organic liquid, the separation, the detection and the data recording can be performed automatically, e.g. controlled by a computer system.

In another embodiment of the present invention, two or more membrane-based extraction units are included in the extraction device with a view to speeding up the sample preparation step.

The total analysis time is 5–120 min, mostly 10–30 min.

EXAMPLE

Extraction of Benzene, Toluene and Xylene from Blood Plasma

A blood plasma sample was analysed by using an extraction device and a method according to the present invention. 0.5 ml spiked blood plasma was pumped into a hydrophobic hollow fibre membrane (Plasmaphan™, Akzo Nobel, Wuppertal, Germany) having an inner diameter of 330 $\mu$m, an outer diameter of 630 $\mu$m, a pore size of 0.2 $\mu$m, a porosity of 70% and an inner volume of 3.2 $\mu$l. The organic liquid constituting the stagnant phase was cyclopentane. After 18.5 mm extraction, the extraction device including a needle was lowered by using a pneumatically controlled piston, and as a result the needle penetrated the septum of a conventional gas chromatograph and was inserted in the injector. A volume of 20 $\mu$l organic liquid containing benzene, toluene and three xylene isomers as analytes was injected. The GC separation was based on standard T-programming and was performed within about 20 mm. During this time, the hollow fibre membrane was regenerated with additional cyclopentane. The total analysis time amounted to about 25 mm. Thus, a new blood plasma sample can be extracted at the same time as the previous sample is analysed. It is evident from the chromatogram, which is free from interfering peaks, that the sample constituents, e.g. protein/-peptides and small charged molecules, were separated from the analytes. The reproducibility of the extraction operation was excellent. The method was also evidently linear, having intercepts which do not significantly differ from origo (95% confidentiality). The detection limit for the analytes is tabulated below.

The concentration enrichment ($E_e$) shows how many times the analytes were concentrated in the membrane based extraction unit.

$E_e(\text{benzene}) \approx 10$ $E_e(\text{toluene}) \approx 15$ $E_e(\text{xylene}) \approx 10$ Test of 0.5 ml blood plasma spiked with 12.5 ppb of benzene, toluene and xylene, extraction during 18.5 min.
Precision of the whole analysis system (RFV):
benzene=18%, toluene=8%, xylene=5%
Precision of the GC (RSD):
benzene=19%, toluene=3%, xylene=6%

Quantitative data (LOD, intercept, RSD).

| Analyte | Intercept | r | LOD (ppb) |
|---|---|---|---|
| Benzene | 860 ± 6500 | 0.9936 | 1 |
| Toluene | 10000 ± 12000 | 0.9952 | 6 |
| Xylene | 2900 ± 6700 | 0.9961 | 2 |

Further, the extraction properties of the hollow fibre membrane were not reduced during the test. No memory effects (carry-over effects) were found during the extraction. Further, it should be noted that the cyclo-pentene was not purified before the test.

Extraction of Benzene, Toluene and Xylene from Urine

This test was performed under the same conditions as the test involving extraction from blood plasma, except that the cyclopentane volume was 1.3 µl and that the injection volume was only 6 µl (splitless). The extraction period was shortened to 15 min, giving a total analysis time of about 20 min. The detection limits were low: benzene 10 ppt (parts per trillion), toluene 4 ppt, and m-xylene 5 ppt. The organic liquid, i.e. cyclopentane, was purified by use of a filter of active carbon. The detection limits are better with a factor of about 1000 compared to the blood plasma test. Compared to the SPME technique, this analysis is by far quicker. Also in this test, good results similar to those in the previous example are obtained.

COMPARATIVE EXAMPLE

A method in which LLE was combined with GC "on-line" to enrich and detect some local anesthetics in blood plasma has been described by Shen, Y., Jonsson, J. A., Mathiasson. L. On-line microporous membrane liquid—liquid extraction for sample pretreatment combined with capillary gas chromatography applied to local anesthetics in blood plasma, Analytical Chemistry, Vol. 70(5), pp 946–953, March 1998.

The approach utilised a hydrophobic membrane as an interfacial support between an aqueous and a hydrophobic liquid.

The sample volume processed was 0.5–1 ml of plasma (or aqueous) samples, and the final transferred volume to the GC was 300 µl of analyte containing solvent.

In the application the sample was continuously pumped on one side of the hydrophobic membrane. Said membrane contained the same solvent as was to be found on the receiving side of the membrane.

Said solvent was also kept in continuous motion[1]. The GC was modified by the implementation of a 7 m long retention gap column[2] and a 3 m long retaining precolumn[3] as well as the 22 m long analytical column. The retaining column and the analytical column were connected over a solvent vapour exit[4], employed to discharge the solvent vapour during the focusing of the analytes. The receiving phase of the membrane was continuously passed through two valves[5], one which was continuously flushed with nitrogen gas (4-port HPLC valve) and the other (10-port HPLC valve) which contained a 400 µl loop[6]. This loop was filled with the receiving phase and upon switching the carrier gas brought the solution onto the modified GC system. After extraction, the loop was flushed with hexane, and later dried with the nitrogen gas mentioned above. The sole purpose of the 4-port valve and the nitrogen gas is then to clean the loop of the 10-port valve.

The volumetric ratio of their system is quite low[7]: 1 ml processed sample with a receiving solvent volume of 400 µl gives at its best a concentration enrichment of 2.5 times. In reality their extraction efficiencies were on an average about 70% from spiked water solutions and between about 30 and 55% (analyte differences) from spiked blood plasma samples. These discrepancies between extraction from different matrices are due to protein binding of analyte in the blood plasma. These figures reveal that the actual concentration enrichment ranged from below 1 (dilution) to about 1.7 times for the best extracted compound in water solution, clearly showing that the approach is to be considered a phase shift and matrix clean-up. The repeatability of the system ranged from 4.6 to 8.7% varying over the different analytes. The major contributor to this was the GC injection[8].

By using the extraction device and the method according to the present invention with a view to enriching and detecting said local anesthetics in blood plasma, the following differences apply:

1 In the present invention the receiving phase is kept stagnant.

2–6 No need for this in the present invention.

7 The volume ratio according to the present invention can be kept nearly as high as desired. In the first application a sample volume of 500 µl was processed and the receiving solvent volume was about 4.5 µl. At its best a concentration enrichment of more than 100 times can be retained. According to the present invention, the same sample volume is processed, but the receiving volume is now 1.5 µl, yielding a volume ratio of 330.

8 This is parallel to the inventor's findings; the extraction protocol itself shows good repeatability and the random errors are introduced with the actual GC-injection of the analyte containing plug.

What is claimed is:

1. A method for extraction of at least one analyte from a sample and transfer of said analyte to a gas chromatography apparatus, comprising the steps of:

providing a volume of at most 5 μl of organic liquid in an organic liquid chamber of an extraction device including a membrane-based extraction unit having an organic liquid chamber of a volume of less than 5 μl for accommodating a stagnant phase of organic liquid, and a sample liquid chamber, said organic liquid chamber and said sample liquid chamber being arranged on opposite sides of a membrane, said sample liquid chamber further having a sample inlet, a sample outlet, said organic liquid chamber further having an organic liquid inlet, the membrane-based extraction unit further including a needle to be connected with a gas chromatography apparatus injector for the transfer of the analyte(s) from the organic liquid chamber to the gas chromatography apparatus, providing a flow of a sample liquid through the sample liquid chamber, whereby the at least one of analyte is extracted from the sample liquid to the organic liquid constituting the stagnant phase, displacing the organic liquid from the membrane-based extraction unit to the gas chromatography apparatus via the needle.

2. A method according to claim 1, comprising the consecutive steps of:

adding the organic liquid to the membrane-based extraction unit and the needle via the organic liquid inlet, wherein the needle bore is essentially filled with the organic liquid, adding a sample via the sample inlet to the membrane-based extraction unit, the analyte(s) being extracted from the sample liquid to the organic liquid constituting the stagnant phase, stopping the flow of the sample after a predetermined period, inserting the needle into an injector of a gas chromatograph, adding additional organic liquid to the membrane-based extraction unit via the organic liquid inlet, thereby regenerating the membrane-based extraction unit and at the same time displacing the stagnant phase containing the analyte extracted into the gas chromatograph apparatus via the needle for subsequent analysis.

3. A method according to claim 1, wherein one or more of the steps are automatic and controlled by a computer system.

4. A method according to claim 1, wherein the organic liquid is gas chromatography compatible and is chosen from the group comprising alcohols, saturated, volatile straight-chain branched or cyclic hydrocarbons, partially unsaturated straight-chain branched or cyclic hydrocarbons, or ethers.

5. A method according to claim 4, wherein the organic liquid is octanol, pentane, hexane, heptane, cyclopentane cyclohexane, cycloheptane, heptene, cyclohexene, diethyl ether, dihexyl ether, carbon disulphide, or carbon tetrachloride.

6. A method according to claim 1, wherein the sample to be analyzed is a physiological liquid chosen from the group consisting of whole blood, urine, sweat, plasma, serum, nasal secrete, cerebrospinal fluid, or is a non-physiological liquid chosen from the group consisting of river water, sea water, lake water, effluent water, influent water, drinking water or a dispersion of any solid matter in aqueous solution including soil samples, food samples, plant samples, tissue samples or aqueous samples of dissolved airborne compounds.

7. A method according to claim 1, wherein the analytes are gas chromatography compatible and are chosen from the group consisting of volatile organic compounds; polyaromatic hydrocarbons, polychlorinated and polybrominated biphenyls, volatile biocides, fatty acids, and fats.

8. The method according to claim 7, wherein the analyte is a volatile organic compound selected from the group consisting of benzene, toluene, and xylene.

9. An extraction device for liquid—liquid extraction of at least one analyte from a sample and transfer of said at least one analyte to a gas chromatography apparatus, said extraction device comprising a membrane-based extraction unit including an organic liquid chamber of a volume of less than 5 μl for accommodating a stagnant phase of organic liquid, and a sample liquid chamber, said organic liquid chamber and said sample liquid chamber being arranged on opposite sides of a membrane, said sample liquid chamber further having a sample inlet, a sample outlet, said organic liquid chamber further having an organic liquid inlet, the membrane-based extraction unit further comprising a needle to be connected with a gas chromatography apparatus injector for the transfer of the analyte(s) from the organic liquid chamber to the gas chromatography apparatus.

10. An extraction device according to claim 9, wherein the needle is integral with the extraction device.

11. An extraction device according to claim 9, further comprising a pump device for feeding the organic liquid via the liquid inlet into the membrane-based extraction unit and a pump device for feeding the sample through the extraction device.

12. An extraction device according to claim 9, wherein the membrane comprises a hydrophobic or hydrophillic membrane.

13. An extraction device according to claim 12, wherein the membrane comprises a hollow fibre membrane.

14. An extraction device according to claim 13 wherein the membrane is essentially cylindrical and vertically arranged.

15. An extraction device according to claim 14 wherein the sample outlet and the organic liquid inlet are located at an upper end and the sample inlet and the organic liquid outlet, which may be directly connected to the needle, are located at a lower end.

16. An extraction device according to claim 12, wherein the membrane is hydrophobic and make of polytetrafluoroethylene (PTFE), polyvinylidenediflouride (PVDF), polypropylene (PP), polyethylene (PE), or silicone rubber.

17. An extraction device according to claim 12, wherein the membrane is hydrophillic and made of cellulose, polyethersulfone, polysulphone, polyacrylonitrile, or polycarbonate.

18. An extraction device according to claim 12, wherein the membrane is a flat membrane or is a hollow fibre membrane.

19. An extraction device according to claim 9, wherein the membrane-based extraction unit has a length of less than about 10 cm.

20. An extraction device according to claim 19, wherein the membrane-based extraction unit has a length of less than about 5 cm.

21. An extraction device according to claim 20 wherein the membrane-based extraction unit has a length of less than about 2 cm.

22. An extraction device according to claim 9, comprising more than one membrane-based extraction unit.

23. A system for gas chromatography analysis of an analyte-containing solvent, comprising an extraction device according to claim 9 and the gas chromatography apparatus.

24. A membrane-based extraction unit for use in an extraction device according to claim 9, wherein the organic liquid chamber has a volume of less than 5 µl for accommodating a stagnant phase of organic liquid, the membrane-based extraction unit further comprising means for receiving the needle to be connected with the gas chromatography apparatus injector for the transfer of the analyte(s) from the organic liquid chamber to the gas chromatography apparatus via the needle.

25. A unit according to claim 24, wherein the membrane is a hydrophobic or hydrophillic membrane.

26. A unit according to claim 25, wherein the membrane is a hollow fibre membrane, the unit being essentially cylindrical and vertically arranged.

27. An extraction device according to claim 26, wherein the sample outlet and the organic liquid inlet are located at an upper end and the sample inlet and the organic liquid outlet, which may be directly connected to the needle, are located at a lower end.

28. A unit according to claim 25, wherein the membrane is hydrophobic and made of polytetrafluoroethylene (PTFE), polyvinylidenediflouride (PVDF), polypropylene (PP), polyethylene (PE), or silicone rubber.

29. A unit according to claim 25, wherein the membrane is hydrophillic and made of cellulose, polyethersulfone, polysulphone, polyacrylonitrile, or polycarbonate.

30. A unit according to claim 24, and having a length of less than about 10 cm.

31. A unit according to claim 30, and having a length of less than about 5 cm.

32. A unit according to claim 31, and having a length of less than about 2 cm.

33. A unit according to claim 24, where the membrane is a flat membrane or a hollow fiber membrane.

* * * * *

UNITED STATES PATENT AND TRADEMARK OFFICE
CERTIFICATE OF CORRECTION

PATENT NO. : 6,623,545 B2 Page 1 of 1
APPLICATION NO. : 10/132711
DATED : September 23, 2003
INVENTOR(S) : Thordarson et al.

It is certified that error appears in the above-identified patent and that said Letters Patent is hereby corrected as shown below:

Column 10, Line 44-47

An extraction device according to claim 12, wherein the membrane is hydrophobic and made of polytetrafluoroethylene (PTFE), polyvinylidenediflouride (PVDF), polypropylene (PP), polyethylene (PE), or silicone rubber.

Column 11, Line 15-19

A unit according to claim 26, wherein the sample outlet and the organic liquid inlet are located at an upper end and the sample inlet and the organic liquid outlet, which may be directly connected to the needle, are located at a lower end.

Signed and Sealed this

Twenty-second Day of August, 2006

JON W. DUDAS
*Director of the United States Patent and Trademark Office*